US011452573B2

(12) United States Patent
Yazdian et al.

(10) Patent No.: US 11,452,573 B2
(45) Date of Patent: Sep. 27, 2022

(54) HANDLE FOR ROBOTIC SURGERY (71) Applicants: Seiedmuhammad Yazdian, Tehran (IR); Alireza Mirbagheri, Tehran (IR); Farzam Farahmand, Tehran (IR)

(72) Inventors: Seiedmuhammad Yazdian, Tehran (IR); Alireza Mirbagheri, Tehran (IR); Farzam Farahmand, Tehran (IR)

(73) Assignee: SINA ROBOTICS AND MEDICAL INNOVATORS CO., Tehran (IR)

( * ) Notice: Subject to any disclaimer, the term of this patent is extended or adjusted under 35 U.S.C. 154(b) by 1040 days.

(21) Appl. No.: 16/139,052

(22) Filed: Sep. 23, 2018

(65) Prior Publication Data
US 2019/0021804 A1 Jan. 24, 2019

Related U.S. Application Data (60) Provisional application No. 62/562,371, filed on Sep. 23, 2017.

(51) Int. Cl.
*A61B 34/00* (2016.01)
*A61B 34/37* (2016.01)
(Continued)

(52) U.S. Cl.
CPC .......... *A61B 34/76* (2016.02); *A61B 17/2909* (2013.01); *A61B 34/35* (2016.02);
(Continued)

(58) Field of Classification Search
CPC ......... A61B 34/76; A61B 34/35; A61B 34/74; A61B 34/37; A61B 17/2909; A61B 2017/00075; A61B 2017/000212; A61B 2017/00398; A61B 2017/2912; B25J 13/025; G05G 5/03
See application file for complete search history.

(56) References Cited

U.S. PATENT DOCUMENTS

| 6,088,020 A | 7/2000 | Mor |
| 8,667,860 B2 | 3/2014 | Helmer et al. |
| 8,994,643 B2 | 3/2015 | Massie et al. |

OTHER PUBLICATIONS

Neupert et al, new device for ergonomic control of a surgical robot with 4 DOF including haptic feedback, Biomedizinische Technik/ Biomedical Engineering, Sep. 2013, DOI: 10.1515/bmt-2013-4404.

*Primary Examiner* — Timothy J Neal
*Assistant Examiner* — William B Chou
(74) *Attorney, Agent, or Firm* — Bajwa IP Law Firm; Haris Zaheer Bajwa (57) ABSTRACT

Disclosed herein a haptic handling system for tele-robotic surgery. The haptic handling system may include a main body, a fine-tuning roll mechanism, and a grasp control mechanism. The main body may include a first hollow cylindrical section and a second hollow cylindrical section. The fine-tuning roll mechanism may include a knob, a roller coupled to the knob, and a roll encoder coupled to the roller. The grasp control mechanism may include a slider comprising an internal slider and an external slider, a lead screw coupled to the slider, and a grasp encoder coupled to the lead screw. The haptic handling system may further include a force feedback system comprising one or more dynamometers measuring a magnitude and a direction of a couple and a force applied to a surgical tool, a roll actuator coupled to the roller, and a grasp actuator coupled to the lead screw.

20 Claims, 8 Drawing Sheets

(51) Int. Cl.
*A61B 17/29* (2006.01)
*A61B 34/35* (2016.01)
*B25J 13/02* (2006.01)
*G05G 5/03* (2008.04)
*A61B 17/00* (2006.01)

(52) U.S. Cl.
CPC ............. *A61B 34/74* (2016.02); *B25J 13/025* (2013.01); *G05G 5/03* (2013.01); *A61B 34/37* (2016.02); *A61B 2017/00075* (2013.01); *A61B 2017/00212* (2013.01); *A61B 2017/00398* (2013.01); *A61B 2017/2912* (2013.01)

HANDLE FOR ROBOTIC SURGERY

CROSS-REFERENCE TO RELATED APPLICATION

This application claims the benefit of priority from U.S. Provisional Patent Application Ser. No. 62/562,371 filed on Sep. 23, 2017, and entitled "ERGONOMIC HANDLE FOR ROBOTIC SURGERY" which is incorporated herein by reference in its entirety.

TECHNICAL FIELD

The present disclosure generally relates to robotic surgery systems, and particularly to an ergonomic handle with haptic feedbacks for robotic surgery.

BACKGROUND

In medical terminology, surgery is, generally, an operation for treating a disease or disorder, for example, by cutting or incising skin, mucosa, and/or other tissues utilizing a medical machine or device. Open abdominal surgery performed by cutting open abdominal skin and treating, forming, or removing internal organs may cause various problems such as bleeding, side effects, patient pain, and/or scars. Accordingly, use of robotic surgery has recently increased aiding in minimizing bleeding and patient pain.

Robotic surgery, in which a robot is controlled from a distance, is an area of robotics that may be useful in various applications, such as in a surgical application. Robotic surgical systems, generally, utilize a surgery robot that consists of a master robot and a slave robot. In robotic surgery, the surgeon directly controls the master robot, which may result in motion of the slave robot that performs the procedure on a patient. The master robot and the slave robot, which are physically separated, may be physically located close to each other (for example in a same room) or remote from each other (for example in different countries).

When a surgery robot is used, a surgeon may be able to access small vessels and nerves, and damp even a minor hand tremor. That is, a precise and stable surgery may be performed. Such characteristics of the surgery robot have enabled successful surgeries for prostate cancer, bladder cancer, renal pelvis cancer, colon cancer, and the like.

In further detail, as a surgeon operates a master robot, the master robot generates and transmits some control signals to a slave robot. Accordingly, the slave robots operates and performs surgery on a patient based on the transmitted control signals. In some cases, the tele-robotic surgery system may provide a facility for the surgeon to make him/her able to monitor a state of the surgery through the master robot.

However, in robotic surgery, the surgeon is not in direct contact with the patient and therefore cannot perform palpation during the surgery. That is, since the surgeon is unable to perceive a degree of contact between a surgery tool mounted to the slave robot and a surgery region of the patient, tissues of the surgery region may be pinched or pulled by the slave robot and thus may be damaged. In addition, the surgeon is unable to detect abnormal tissues through palpation. In other words there is not any haptic feedback for the surgeon during the surgery.

On the other hand, most handle designs and configurations known in the art are not shaped to properly conform to the human hand or augment the tool's use or purpose. The known tool handles instead follow a historic lineage of geometric shapes with slight variation and color changes. The variety of handle designs available today would indicate that the hand must adapt to the handle shape rather than the handle conforming to the hand shape. There is, therefore, a need for an ergonomic handle with haptic feedbacks for robotic surgeries.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to an exemplary embodiment, the present disclosure describes a handle for tele-robotic surgery. In an exemplary embodiment, the handle may include a main body, a fine-tuning roll mechanism, and a grasp control mechanism.

In an exemplary embodiment, the main body may include a first hollow cylindrical section and a second hollow cylindrical section. In an exemplary embodiment, the first hollow cylindrical section may include a hollow cylindrical-shaped structure and a sectoral slot on a shell of the first hollow cylindrical section. In an exemplary embodiment, the second hollow cylindrical section may include a hollow cylindrical-shaped structure and a longitudinal slot on a shell of the second hollow cylindrical section. In an exemplary embodiment, the first hollow cylindrical section may be attached to the second hollow cylindrical section.

In an exemplary embodiment, the fine tuning roll mechanism may include a knob mounted rotatably around the main body. The fine tuning roll mechanism may further include a roller coupled to the knob. In an exemplary embodiment, the roller may be configured to rotate responsive to a rotation of the knob about a first axis.

In an exemplary embodiment, the fine-tuning roll mechanism may further include a roll encoder coupled to the roller. In an exemplary embodiment, the roll encoder may be configured to transmit a first set of data to one or more processors associated with the rotation of the knob.

In an exemplary embodiment, the grasp control mechanism may include a slider, a lead screw, and a grasp encoder. In an exemplary embodiment, the slider may include an external slider mounted slidably around the main body, and an internal slider disposed slidably inside the main body. In one or more embodiments, the internal slider may be coupled to the external slider. The internal slider may be configured to slide along a second axis responsive to a linear movement of the external slider along the second axis.

In an exemplary embodiment, the lead screw may include a cylindrical structure. The lead screw may be coupled to the internal slider. Furthermore, the lead screw may be configured to rotate about the second axis responsive to the linear movement of the external slider.

In an exemplary embodiment, the grasp encoder may be coupled to the lead screw, and the grasp encoder may be configured to transmit a second set of data to the one or more processors associated with the linear movement of the external slider.

In an exemplary embodiment, the knob may include a hollow cylindrical structure and the knob may be mounted rotatably around the first cylindrical section. In an exemplary embodiment, the knob may be configured to rotate about the first axis.

In an exemplary embodiment, the roller may include a first cylindrical section and a second cylindrical section. In an exemplary embodiment, the first cylindrical section may be connected to the second cylindrical section utilizing a connecting rod. In an exemplary embodiment, the first cylindrical section may be disposed rotatably inside the sectoral slide. Furthermore, the first cylindrical section may be configured to rotate around a longitudinal axis of the roller. In an exemplary embodiment, the first cylindrical section may also be frictionally engaged with an interior surface of the knob.

In an exemplary embodiment, the external slider may include a hollow cylindrical-shaped structure. In an exemplary embodiment, the internal slider may also include a hollow cylindrical-shaped structure. In an exemplary embodiment, the external slider may be mounted slidably around the second hollow cylindrical section and the external slider may be configured to slide along the first axis. In an exemplary embodiment, the internal slider may be attached to the external slider utilizing a plurality of screws through the longitudinal slot.

In an exemplary embodiment, the internal slider may include an internally threaded section on an interior surface of the internal slider and the lead screw may be disposed rotationally and slidably inside the main body. Furthermore, the lead screw may be configured to rotate around the second axis responsive to a linear movement of the internal slider along the second axis. The lead screw may include an externally threaded section on an exterior surface of the lead screw. In an exemplary embodiment, the internally threaded section may be configured to mesh with the externally threaded section.

In an exemplary embodiment, the first axis may correspond to a longitudinal axis of the cylindrical-shaped structure of the first hollow cylindrical section. The second axis may also correspond to a longitudinal axis of the cylindrical-shaped structure of the second cylindrical structure. In an exemplary embodiment, the second axis may be the same as the first axis.

In an exemplary embodiment, the grasp encoder may be coupled to the lead screw utilizing a cylindrical-shaped coupling. In an exemplary embodiment, the cylindrical-shaped coupling may include a lead screw insertion hole located at a proximal end of the cylindrical-shaped coupling and a grasp encoder insertion hole located at a distal end of the cylindrical-shaped coupling. Furthermore, a size of the lead screw insertion hole may correspond to a size of the lead screw, and a size of the grasp encoder insertion hole may correspond to a size of the grasp encoder.

According to an exemplary embodiment, the present disclosure describes a haptic handling system for telerobotic surgery. In an exemplary embodiment, the haptic handling system may include a handle and a force feedback system. In an exemplary embodiment, the handle may include a main body, a fine-tuning roll mechanism, and a grasp control mechanism.

In an exemplary embodiment, the main body may include a first hollow cylindrical section and a second hollow cylindrical section. In an exemplary embodiment, the first hollow cylindrical section may include a hollow cylindrical-shaped structure and a sectoral slot on a shell of the first hollow cylindrical section. In an exemplary embodiment, the second hollow cylindrical section may include a hollow cylindrical-shaped structure and a longitudinal slot on a shell of the second hollow cylindrical section. In an exemplary embodiment, the first hollow cylindrical section may be attached to the second hollow cylindrical section.

In an exemplary embodiment, the fine tuning roll mechanism may include a knob mounted rotatably around the main body and the fine tuning roll mechanism may further include a roller coupled to the knob. In an exemplary embodiment, the roller may be configured to rotate responsive to a rotation of the knob about a first axis.

In an exemplary embodiment, the fine-tuning roll mechanism may further include a roll encoder coupled to the roller. In an exemplary embodiment, the roll encoder may be configured to transmit a first set of data to one or more processors associated with the rotation of the knob.

In an exemplary embodiment, the grasp control mechanism may include a slider, a lead screw, and a grasp encoder. In an exemplary embodiment, the slider may include an external slider mounted slidably around the main body, and an internal slider disposed slidably inside the main body. In an exemplary embodiment, the internal slider may be coupled to the external slider. In an exemplary embodiment, the internal slider may be configured to slide along a second axis responsive to a linear movement of the external slider along the second axis.

In an exemplary embodiment, the lead screw may include a cylindrical structure and the lead screw may be coupled to the internal slider. Furthermore, the lead screw may be configured to rotate about the second axis responsive to the linear movement of the external slider.

In an exemplary embodiment, the grasp encoder may be coupled to the lead screw and the grasp encoder may be configured to transmit a second set of data to the one or more processors associated with the linear movement of the external slider. In an exemplary embodiment, the knob may include a hollow cylindrical structure. In an exemplary embodiment, the knob may be mounted rotatably around the first cylindrical section and the knob may be configured to rotate about the first axis.

In an exemplary embodiment, the roller may include a first cylindrical section and a second cylindrical section and the first cylindrical section may be connected to the second cylindrical section utilizing a connecting rod. In an exemplary embodiment, the first cylindrical section may be disposed rotatably inside the sectoral slide. Furthermore, the first cylindrical section may be configured to rotate around a longitudinal axis of the roller and furthermore, the first cylindrical section may also be frictionally engaged with an interior surface of the knob.

In an exemplary embodiment, the external slider may include a hollow cylindrical-shaped structure and the internal slider may also include a hollow cylindrical-shaped structure. In an exemplary embodiment, the external slider may be mounted slidably around the second hollow cylindrical section and also the external slider may be configured to slide along the first axis. In an exemplary embodiment, the internal slider may be attached to the external slider utilizing a plurality of screws through the longitudinal slot.

In an exemplary embodiment, the internal slider may include an internally threaded section on an interior surface of the internal slider and the lead screw may be disposed rotationally and slidably inside the main body. In an exemplary embodiment, the lead screw may be disposed rotationally and slidably inside the main body. Furthermore, the lead screw may be configured to rotate around the second axis responsive to a linear movement of the internal slider along the second axis. In an exemplary embodiment, the lead screw may include an externally threaded section on an exterior surface of the lead screw. Furthermore, the internally threaded section may be configured to mesh with the externally threaded section.

In an exemplary embodiment, the first axis may correspond to a longitudinal axis of the cylindrical-shaped structure of the first hollow cylindrical section and the second axis may also correspond to a longitudinal axis of the cylindrical-shaped structure of the second cylindrical structure. In an exemplary embodiment, the second axis may be the same as the first axis.

In an exemplary embodiment, the grasp encoder may be coupled to the lead screw utilizing a cylindrical-shaped coupling. The cylindrical-shaped coupling may include a lead screw insertion hole located at a proximal end of the cylindrical-shaped coupling and a grasp encoder insertion hole located at a distal end of the cylindrical-shaped coupling. Furthermore, a size of the lead screw insertion hole may correspond to a size of the lead screw, and a size of the grasp encoder insertion hole may correspond to a size of the grasp encoder.

In an exemplary embodiment, the force feedback system may include one or more dynamometers measuring a magnitude and a direction of a couple and a magnitude and a direction of a force applied to a surgical tool. In an exemplary embodiment, the force feedback system may include a roll actuator coupled to the roller, and a grasp actuator coupled to the lead screw. In an exemplary embodiment, responsive to a rotational movement of the roll actuator, the knob rotates around the first axis, and responsive to a rotational movement of the grasp actuator, the external slider moves linearly along the second axis.

In an exemplary embodiment, the one or more processors are further configured to transmit a third set of data to the roll actuator based on the magnitude and the direction of the couple measured utilizing the one or more dynamometers and also are configured to transmit a fourth set of data to the grasp actuator based on the magnitude and the direction of the force measured utilizing the one or more dynamometers.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Herein is disclosed an exemplary handle and an exemplary handling system for tele-robotic surgery. The exemplary handle provides an ergonomic facility for a surgeon to control a surgical tool utilizing a tele-robotic surgical system. The exemplary handle provides a facility for the surgeon to move the surgical tool in direction of two degrees of freedom. Furthermore, the exemplary handling system provides the surgeon with the exemplary handle along with a facility for receiving haptic feedbacks from the surgical tool.

The exemplary handling system, in addition to an exemplary handle, may include a number of dynamometers. The dynamometers may measure magnitudes and directions of a force and a couple applied to the surgical tool. The exemplary handling system may also include a processing unit. The processing unit, apart from various other processes, may receive data and transmit commands associated with haptic feedbacks to the surgeon's hand based on the measured magnitudes and directions of the force and the couple by the dynamometers.

Figure 1A:
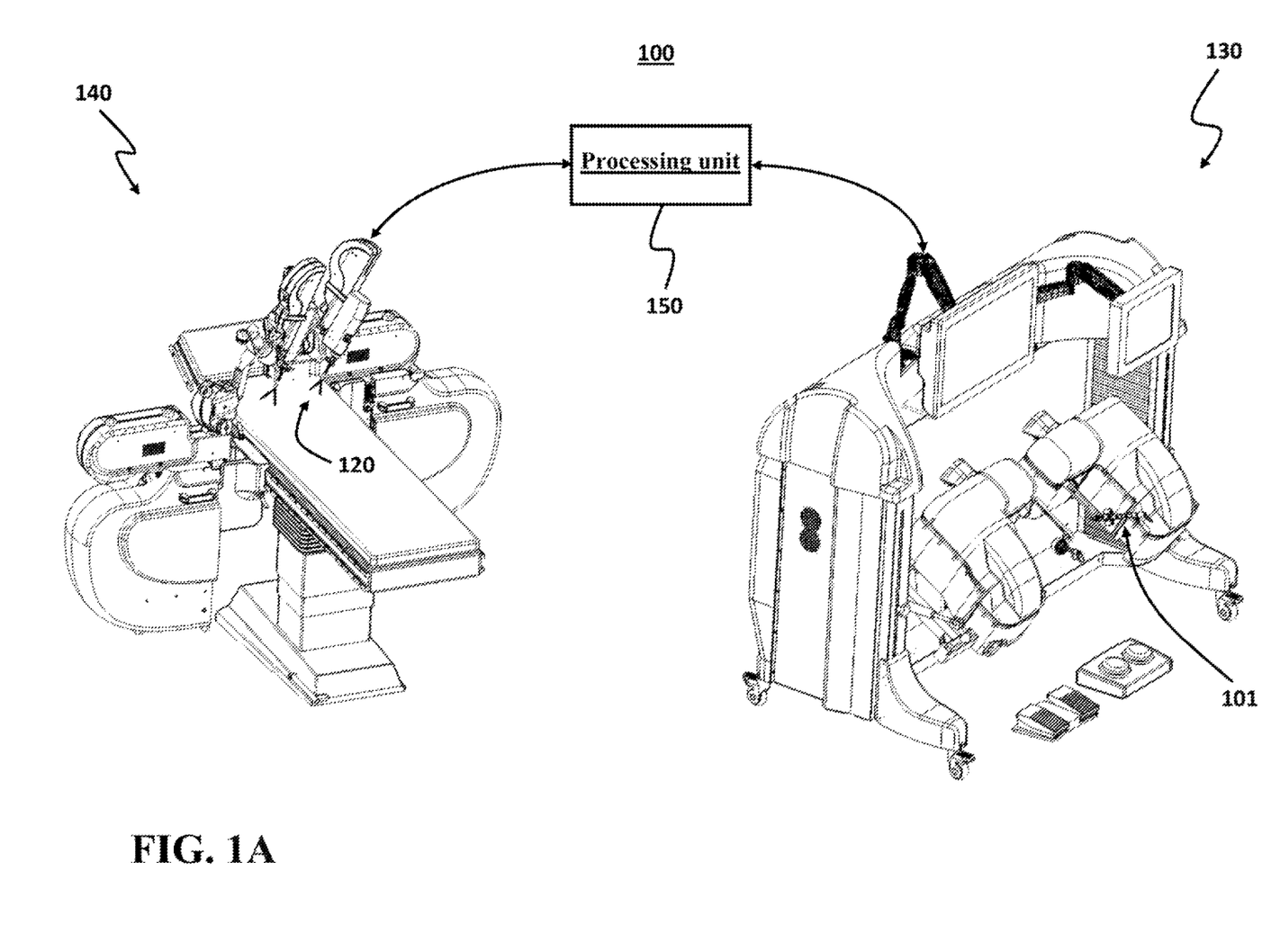
FIG. 1A illustrates a tele-robotic surgical system, consistent with one or more exemplary embodiments of the present disclosure.

FIG. 1 shows an exemplary tele-robotic surgical system, consistent with one or more exemplary embodiments of the present disclosure. In an exemplary embodiment, the tele-robotic surgical system 100 may include a master robot 130, a slave robot 140, and a processing unit 150. In an exemplary embodiment of the present disclosure, the master robot 130 may include a handle 10*al*, and slave robot 140 may include a surgical tool 120. In an exemplary embodiment, the surgeon may control surgical tool 120 utilizing master robot 130, slave robot 140, and processing unit 150. In an exemplary embodiment, handle 101 may transmit commands associated with the surgeon hand movements to processing unit 150 utilizing master robot 130. Thereafter, processing unit 150 may process the transmitted commands from handle 101 and accordingly may transmit commands associated with movement of surgical tool 120 to surgical tool 120 utilizing slave robot 140.

Figure 1B:
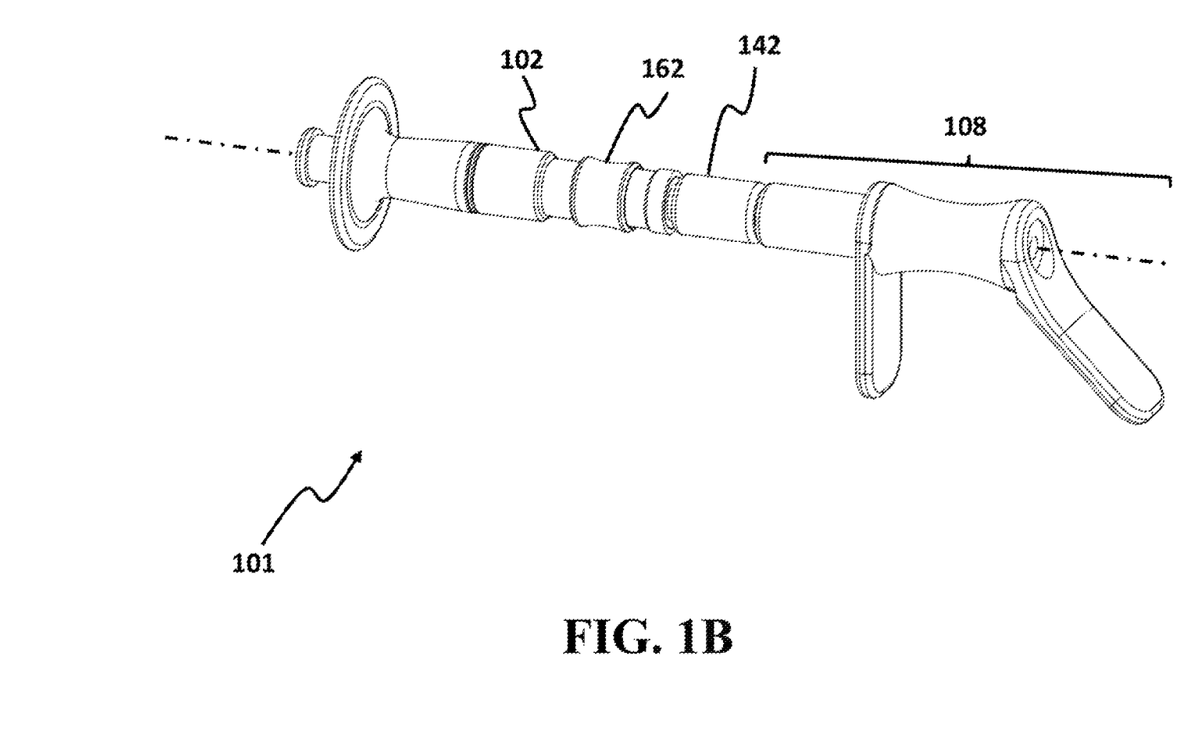
FIG. 1B illustrates a perspective view of a handle for a tele-robotic surgery, consistent with one or more exemplary embodiments of the present disclosure.
Figure 1C:
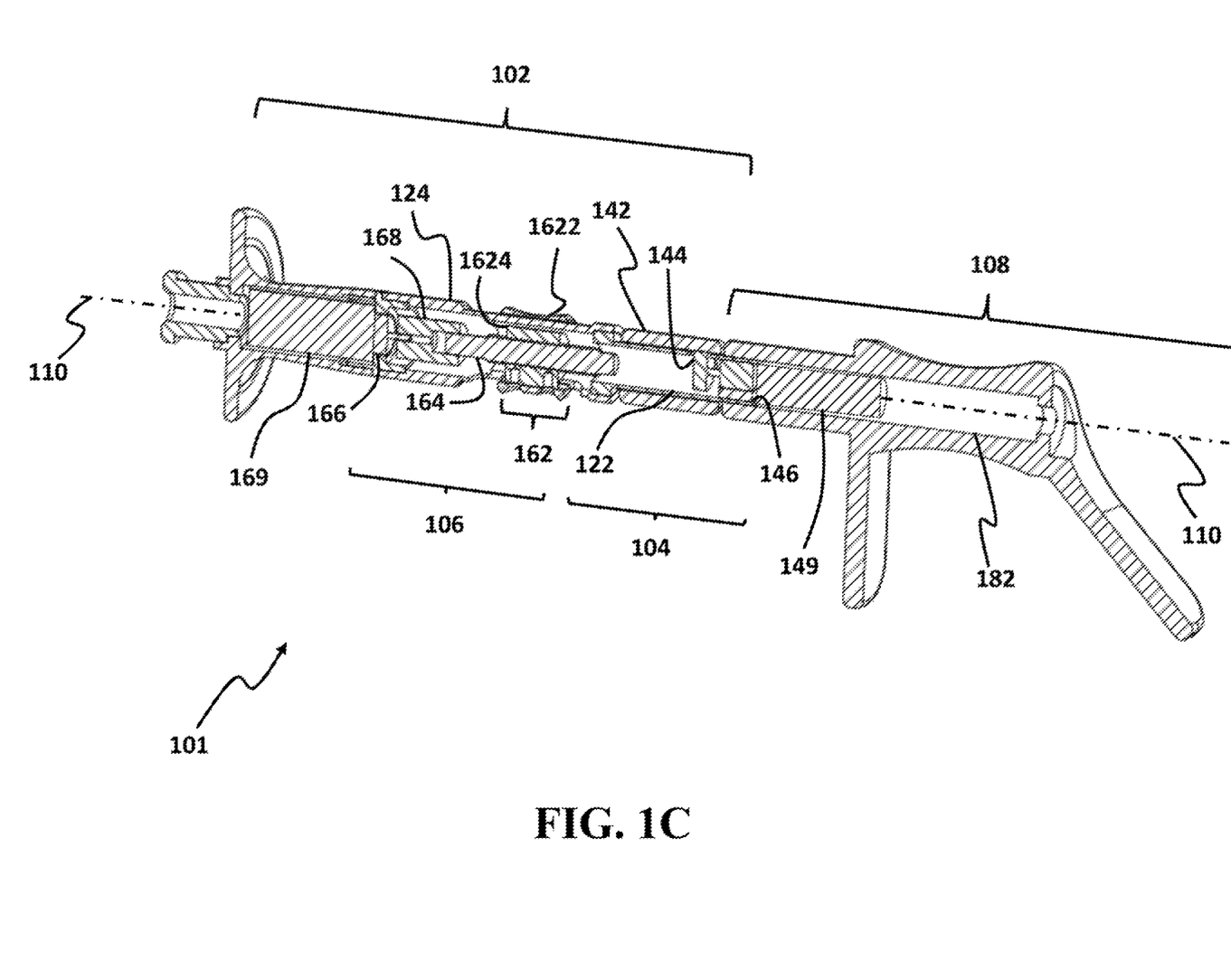
FIG. 1C illustrates a sectional perspective view of a handle for a tele-robotic surgery, consistent with one or more exemplary embodiments of the present disclosure.

FIG. 1B shows a perspective view of an exemplary handle for an exemplary tele-robotic surgery, consistent with one or more exemplary embodiments of the present disclosure. FIG. 1C shows a sectional view of an exemplary handle for an exemplary tele-robotic surgery, consistent with an exemplary embodiment of the present disclosure. In an exemplary embodiment, as shown in FIGS. 1B and 1C, handle 101 may include a main body 102, a fine-tuning roll mechanism 104, and a grasp control mechanism 106. In an exemplary embodiment, handle 101 may further include a cuff 108 located at a distal end of handle 101. In one exemplary embodiment, cuff 108 may be sized to adapt to a size of a surgeon's hand. Furthermore, cuff 108 may include a longitudinal hole 182. It may be understood that longitudinal hole 182 may provide benefits including but not limited to a decrease in an exemplary handle's weight and consequently may provide a facility for the surgeon to use and carry handle 101 more easily. In an exemplary embodiment, cuff 108 may provide a facility for the surgeon to adapt size of handle 101 to a size of his/her hand. For example, in an exemplary embodiment, cuff 108 may be able to be moved and/or fixed along a first axis 110 to alter a size of handle 101. In an exemplary embodiment, cuff 108 may provide significant benefits including but not limited to an increase in stability of handle 101 during the surgery. In fact, cuff 108 may help handle 101 to be maintained in the surgeries' hand under forces and stresses during the surgery.

Figure 2:
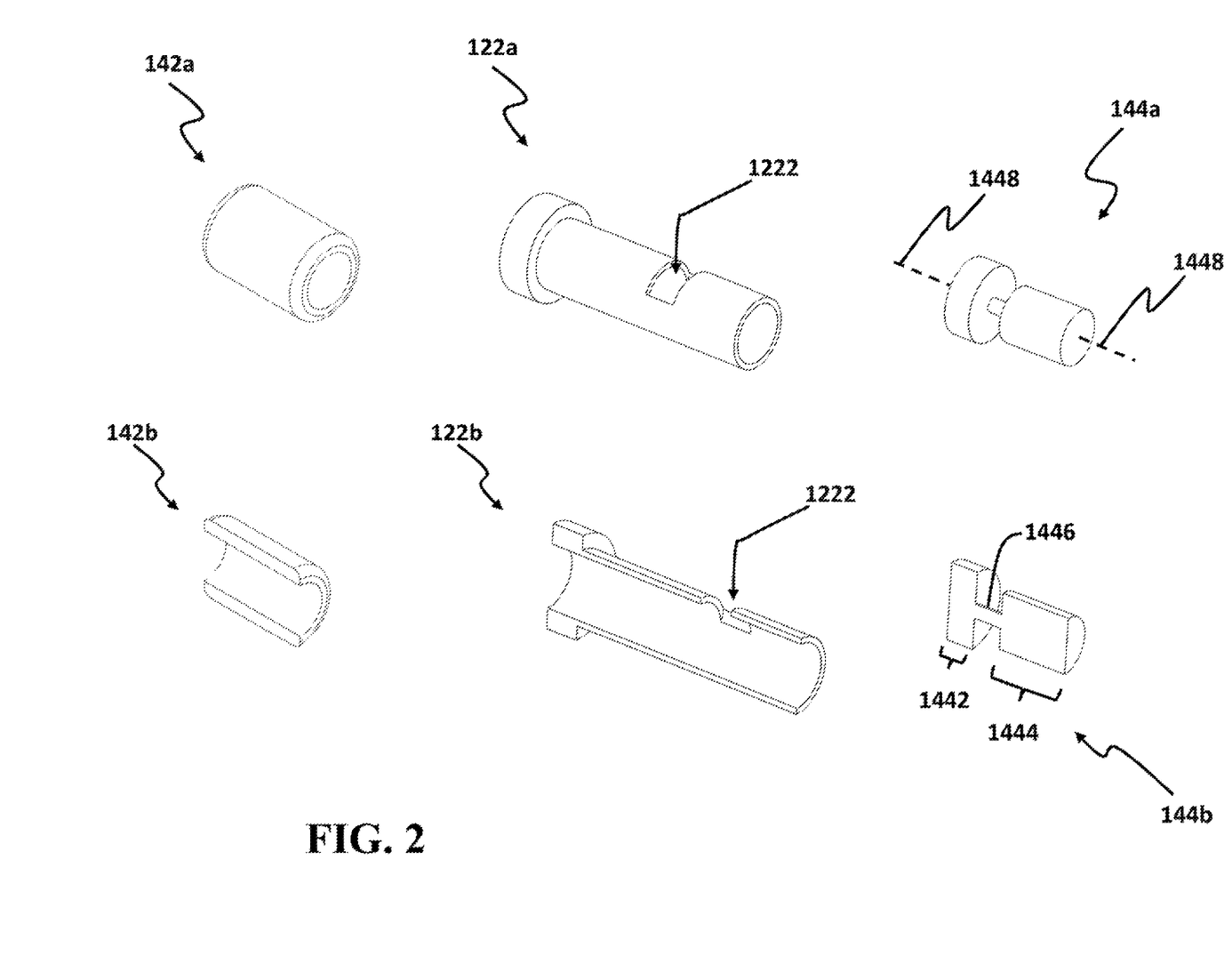
FIG. 2 illustrates an exploded view of a fine-tuning roll mechanism of a handle, consistent with one or more exemplary embodiments of the present disclosure.
Figure 4:
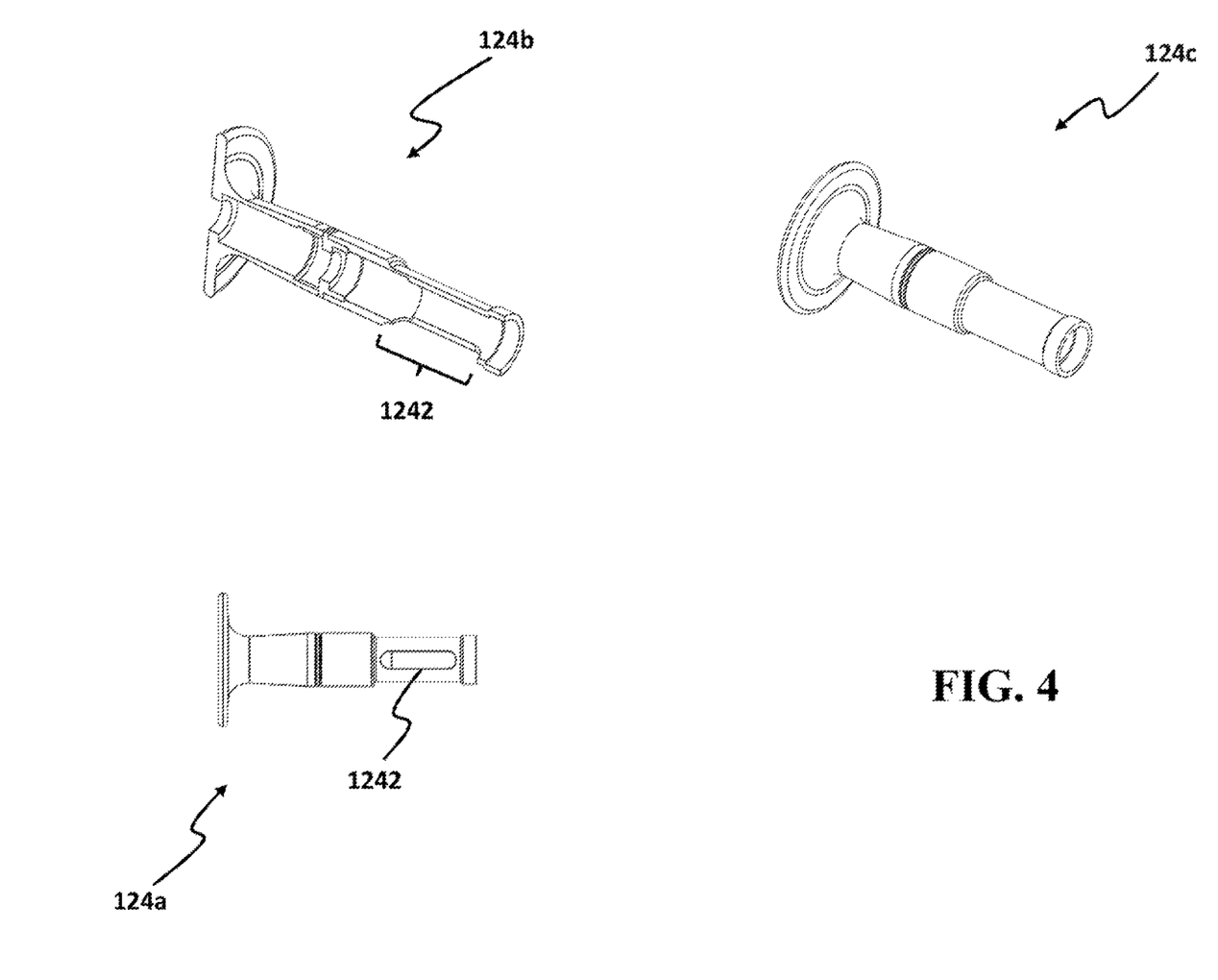
FIG. 4 illustrates a perspective view, a sectional view, and a side view of a handle, consistent with one or more exemplary embodiments of the present disclosure.

In an exemplary embodiment, main body 102 may include a first hollow cylindrical section 122 and a second hollow cylindrical section 124. FIG. 2 shows an exploded view of a fine-tuning roll mechanism of a handle, consistent with one or more exemplary embodiments of the present disclosure. As shown in FIG. 2, perspective view 122a of hollow cylindrical section 122 and sectional view 122b of hollow cylindrical section 122 illustrate that first hollow cylindrical section 122 may include a hollow cylindrical-shaped structure and a sectoral slot 1222 on a shell of first hollow cylindrical section 122. FIG. 4 shows a perspective view, a sectional view, and a side view of a handle, consistent with one or more exemplary embodiments of the present disclosure. As shown in FIG. 4, side view 124a, sectional view 124b, and perspective view 124c illustrate that second hollow cylindrical section 124 may include a hollow cylindrical-shaped structure and a longitudinal slot 1242 on a shell of second hollow cylindrical section 124. As shown in FIG. 1C, in an exemplary embodiment, first hollow cylindrical section 122 may be attached to second hollow cylindrical section 124. In an exemplary embodiment, first hollow cylindrical section 122 and second hollow cylindrical section 124 may be manufactured with some threaded sections thereof that allow them to be attached to each other through a screw mechanism. In an exemplary embodiment, first hollow cylindrical section 122 and second hollow cylindrical section 124 may be attached to each other utilizing at least one of a plurality of screws, a welding mechanism, and any other mechanisms with similar functionality. In an exemplary embodiment, first hollow cylindrical section 122 and second hollow cylindrical section 124 may be manufactured seamlessly in order to constitute a unique or unitary/integral part.

As illustrated in FIG. 1C and FIG. 2, in an exemplary embodiment, fine tuning roll mechanism 104 may include a knob 142 mounted rotatably around main body 102. As shown in FIG. 2, perspective view 142a of knob 142, and sectional view 142b of knob 142 illustrate that knob 142 may be a hollow cylindrical structure. In an exemplary embodiment, fine tuning roll mechanism 104 may further include a roller 144 coupled to knob 142. In an exemplary embodiment, roller 144 may rotate around a longitudinal axis 1448 of roller 144 responsive to a rotation of knob 142 about first axis 110. For purpose of reference, it may be understood that, in some exemplary embodiments, first axis 110 may be the same as a longitudinal axis of main body 102.

As shown in FIG. 1C, perspective view 144a of roller 144 and sectional view 144b of roller 144 illustrated that, in an exemplary embodiment, fine-tuning roll mechanism 104 may further include a roll encoder 146 coupled to roller 144. In an exemplary embodiment, roll encoder 146 may transmit a first set of data to processing unit 150 associated with the rotation of the knob. In an exemplary embodiment, the first set of data may include data related to or associated with roller 144 rotation amount, roller 144 rotation rate, and roller 144 rotation direction.

In an exemplary embodiment, as shown in FIG. 2, knob 142 may include a hollow cylindrical structure. In an exemplary embodiment, knob 142 may be mounted rotatably around first cylindrical section 122 and also knob 142 may rotate about first axis 110. In an exemplary embodiment, roller 144 may include a first cylindrical section 1442 and a second cylindrical section 1444. In an exemplary embodiment, first cylindrical section 1442 may be connected to second cylindrical section 1444 utilizing a connecting rod 1446. In an exemplary embodiment, first cylindrical section 1442, second cylindrical section 1444, and connecting rod 1446 may be manufactured seamlessly or connected with each other in order to constitute a unique or unitary/integral part. In an exemplary embodiment, first cylindrical section 1442 may be disposed rotatably inside sectoral slide 1222. Furthermore, first cylindrical section 1442 may be configured to rotate around a longitudinal axis 1448 of roller 144. In an exemplary embodiment, for purpose of coupling, first cylindrical section 1442 may also be frictionally engaged with an interior surface of knob 142. In an exemplary embodiment, first cylindrical section 1442 may be coupled to knob 142 via a gear mechanism, a pulley/belt mechanism, and/or any other mechanism with similar functionality.

For purpose of reference, it may be understood that, in an exemplary embodiment, responsive to the surgeon rolling the knob 142, roll encoder 146 may measure amount, rate, and direction of knob 142 rotation and then may transmit a set of knob data to processing unit 150. In an exemplary embodiment, the set of knob data may include data related to or associated with knob 142 rotation amount, knob 142 rotation rate, and knob 142 rotation direction. Thereafter, processing unit 150 may transmit commands to surgical tool 120 associated with amount, rate, and direction of the rotation that surgical tool 120 may be supposed to do.

Figure 3:
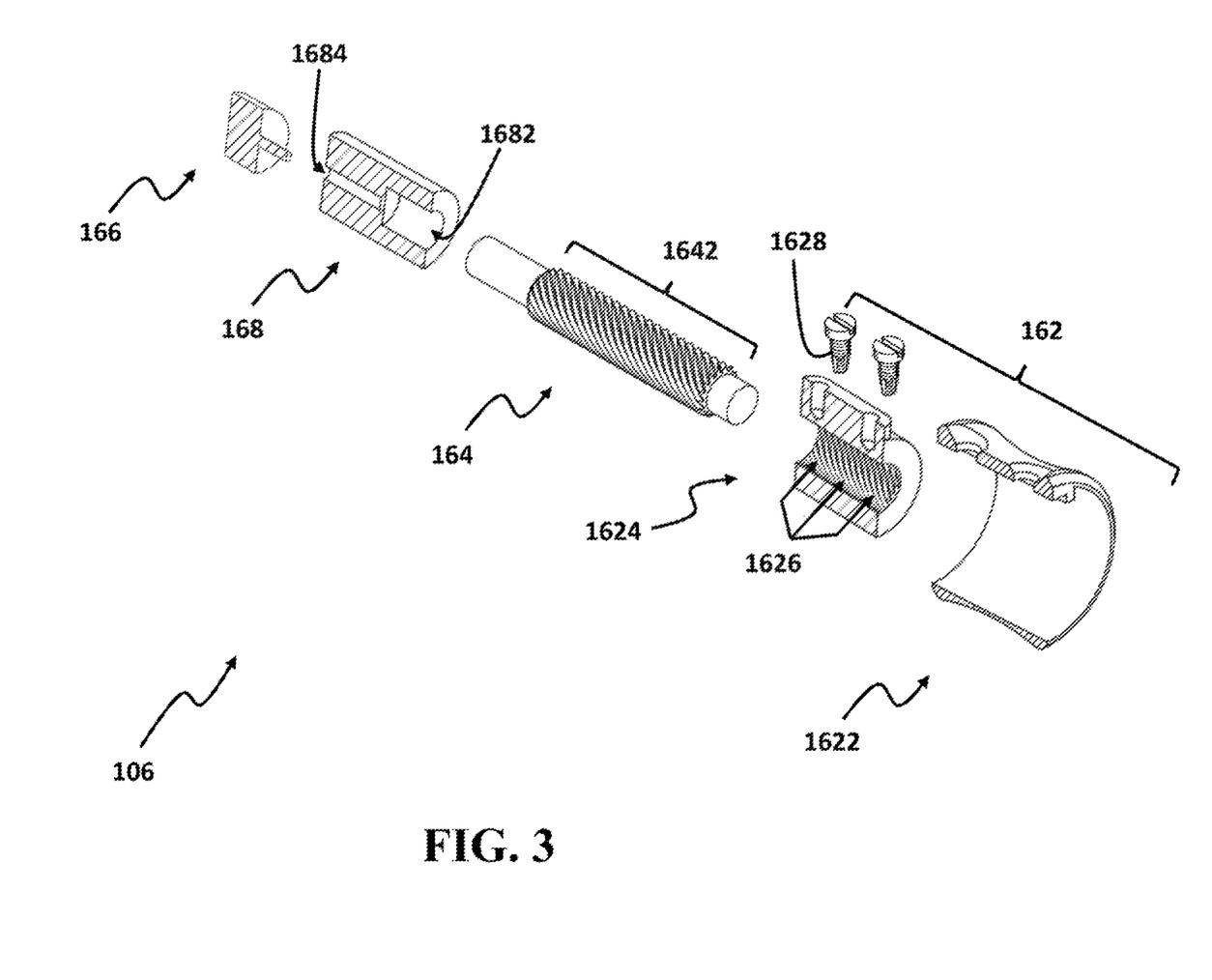
FIG. 3 illustrates an exploded view of a grasp control mechanism of a handle, consistent with one or more exemplary embodiments of the present disclosure.

FIG. 3 shows an exploded view of grasp control mechanism 106 of handle 101, consistent with one or more exemplary embodiments of the present disclosure. In an exemplary embodiment, grasp control mechanism 106 may include a slider 162, a lead screw 164, and a grasp encoder 166. In an exemplary embodiment, slider 162 may include an external slider 1622 mounted slidably around main body 102, and an internal slider 1624 disposed slidably inside main body 102. In an exemplary embodiment, internal slider 1624 may be coupled to external slider 1622 in a way such that internal slider 1624 slides along a second axis responsive to a linear movement of external slider 1622 along the second axis. In an exemplary embodiment, the second axis may be the same as first axis 110.

In an exemplary embodiment, as shown in FIG. 3, lead screw 164 may be a cylindrical structure, and lead screw 164 may be coupled to internal slider 1624. Furthermore, lead screw 164 may rotate about the second axis responsive to the linear movement of external slider 1622.

In an exemplary embodiment, internal slider 1624 may include an internally threaded section 1626 on an interior surface of internal slider 1624. In an exemplary embodiment, lead screw 164 may be disposed rotationally and slidably inside main body 102. Lead screw 164 may include an externally threaded section 1642 on an exterior surface of lead screw 164. In an exemplary embodiment, internally threaded section 1626 may be meshed with externally threaded section 1642. Furthermore, lead screw 164 may be configured to rotate around the second axis responsive to a linear movement of internal slider 1624 along the second axis.

In an exemplary embodiment, grasp encoder 166 may be coupled to lead screw 164. Furthermore, grasp encoder 166 may transmit a second set of data to processing unit 150 associated with the linear movement of the external slider. In an exemplary embodiment, the second set of data may include data related to or associated with lead screw 164 rotation amount, lead screw 164 rotation rate, and lead screw 164 rotation direction. In an exemplary embodiment, external slider 1622 may include a hollow cylindrical-shaped structure. Similarly, internal slider 1624 may also include a hollow cylindrical-shaped structure. In an exemplary embodiment, external slider 1622 may be mounted slidably around second hollow cylindrical section 124. Furthermore, external slider 1622 may slide along first axis 110. In an exemplary embodiment, internal slider 1624 may be attached to external slider 1622 utilizing a plurality of screws 1628 through longitudinal slot 1242.

In an exemplary embodiment, the surgeon may slide external slider 1622 and then grasp encoder 166 may transmit the second set of data to processing unit 150 based on the amount, rate, and direction of lead screw 164 rotation measured by grasp encoder 166. Thereafter, processing unit 150 may transmit commands to surgical tool 120 associated with amount, rate, and direction of the grasp that surgical tool 120 may be supposed to apply.

In an exemplary embodiment, grasp encoder 166 may be coupled to lead screw 164 utilizing a cylindrical-shaped coupling 168. In an exemplary embodiment, cylindrical-shaped coupling 168 may include a lead screw insertion hole 1682 located at a proximal end of cylindrical-shaped coupling 168 and a grasp encoder insertion hole 1684 located at a distal end of cylindrical-shaped coupling 168. In an exemplary embodiment, a size of lead screw insertion hole 1682 may correspond to a size of lead screw 164, and a size of grasp encoder insertion hole 1684 may correspond to a size of grasp encoder 166. In an exemplary embodiment, the diameter of lead screw 164 may be substantially equal to the diameter of lead screw insertion hole 1682. In an exemplary embodiment, lead screw 164 may be press fitted inside lead screw insertion hole 1682. In an exemplary embodiments, the diameter of grasp encoder 166 may be substantially equal to the diameter of grasp encoder insertion hole 1684. In an exemplary embodiment, grasp encoder 166 may be press fitted inside grasp encoder insertion hole 1684.

In another aspect of the present disclosure, an exemplary haptic handling system for tele-robotic surgery is disclosed. In an exemplary embodiment, the haptic handling system may include a handle and a force feedback system. In an exemplary embodiment, the handle of the exemplary haptic handling system may be substantially analogous to an exemplary handle 101 shown in FIG. 1A, 1B, and FIG. 1C. As shown in FIG. 1C, an exemplary embodiment handle 101 may include a main body 102, a fine-tuning roll mechanism 104, and a grasp control mechanism 106. In an exemplary embodiment, handle 101 may further include a cuff 108 located at a distal end of handle 101. In an exemplary embodiment, cuff 108 may be sized to adapt to a size of the surgeon's hand. Furthermore, cuff 108 may include a longitudinal hole 182. It may be understood that longitudinal hole 182 may provide numerous benefits including, but not limited to, a decrease in a handle's weight and consequently may therefore provide a facility for the surgeon to use and carry handle 101 more easily. In an exemplary embodiment, cuff 108 may provide a facility for the surgeon to adapt size of handle 101 to a size of his/her hand. For example, in an exemplary embodiment, cuff 108 may be able to be moved and/or fixed along a first axis 110 to alter a size of handle 101. In an exemplary embodiment, cuff 108 may provide significant benefits including but not limited to an increase in stability of handle 101 during the surgery. In fact, cuff 108 may help handle 101 to be maintained in the surgeries' hand under forces and stresses during the surgery.

In an exemplary embodiment, main body 102 may include a first hollow cylindrical section 122 and a second hollow cylindrical section 124. In an exemplary embodiment, as shown in FIG. 2, first hollow cylindrical section 122 may include a hollow cylindrical-shaped structure and a sectoral slot 1222 on a shell of first hollow cylindrical section 122. In an exemplary embodiment, as shown in FIG. 4, second hollow cylindrical section 124 may include a hollow cylindrical-shaped structure and a longitudinal slot 1242 on a shell of second hollow cylindrical section 124. As shown in FIG. 1C, in an exemplary embodiment, first hollow cylindrical section 122 may be attached to second hollow cylindrical section 124. For example, first hollow cylindrical section 122 and second hollow cylindrical section 124 may be manufactured with some threaded sections thereof that provide them a facility to be attached to each other through a screw mechanism. In an exemplary embodiment, first hollow cylindrical section 122 and second hollow cylindrical section 124 may be attached to each other utilizing at least one of a plurality of screws, a welding mechanism, and any other mechanisms with similar functionality. In an exemplary embodiment, first hollow cylindrical section 122 and second hollow cylindrical section 124 may be manufactured seamlessly in order to constitute a unique or unitary/integral part.

As illustrated in FIG. 1C and FIG. 2, in an exemplary embodiment, fine tuning roll mechanism 104 may include a knob 142 mounted rotatably around main body 102. In an exemplary embodiment, fine tuning roll mechanism 104 may further include a roller 144 coupled to knob 142. In an exemplary embodiment, roller 144 may rotate responsive to a rotation of knob 142 about a first axis 110. For purpose of reference, it may be understood that, in an exemplary embodiment, first axis 110 may be the longitudinal axis of main body 102.

In an exemplary embodiment, as shown in FIG. 1C, fine-tuning roll mechanism 104 may further include a roll encoder 146 coupled to roller 144. In an exemplary embodiment, roll encoder 146 may transmit a first set of data to processing unit 150 associated with the rotation of the knob. In an exemplary embodiment, the first set of data may include data related to or associated with roller 144 rotation amount, roller 144 rotation rate, and roller 144 rotation direction.

In an exemplary embodiment, as shown in FIG. 2, knob 142 may include a hollow cylindrical structure. In an exemplary embodiment, knob 142 may be mounted rotatably around first cylindrical section 122 and also knob 142 may be configured to rotate about first axis 110. In an exemplary embodiment, roller 144 may include a first cylindrical section 1442 and a second cylindrical section 1444. In an exemplary embodiment, first cylindrical section 1442 may be connected to second cylindrical section 1444 utilizing a connecting rod 1446. In an exemplary embodiment, first cylindrical section 1442, second cylindrical section 1444, and connecting rod 1446 may be manufactured seamlessly in order to constitute a unique or unitary/integral part. In an exemplary embodiment, first cylindrical section 1442 may be disposed rotatably inside sectoral slide 1222. Furthermore, first cylindrical section 1442 may be configured to rotate around a longitudinal axis 1448 of roller 144. In an exemplary embodiment, for purpose of coupling, first cylindrical section 1442 may also be frictionally engaged with an interior surface of knob 142. In an exemplary embodiment, first cylindrical section 1442 may be coupled to knob 142 via a gear mechanism, a pulley/belt mechanism, and/or any other mechanism with similar functionality.

In an exemplary embodiment, the surgeon may roll knob 142 and roll encoder 146 may measure amount, rate, and direction of knob 142 rotation and then may transmit a first set of data to processing unit 150. In an exemplary embodiment, the first set of data may include data associated with or related to knob 142 rotation amount, knob 142 rotation rate, and knob 142 rotation direction. Thereafter, processing unit 150 may transmit commands to surgical tool 120 associated with amount, rate, and direction of the rotation that surgical tool 120 may be supposed to do.

In an exemplary embodiment, processing unit may generate commands for surgical tool 120 based on received data including, for example, first or second set of data or any other data reflecting surgeon input.

FIG. 3 shows an exploded view of grasp control mechanism 106 of handle 101, consistent with an exemplary embodiment of the present disclosure. In an exemplary embodiment, grasp control mechanism 106 may include a slider 162, a lead screw 164, and a grasp encoder 166. In an exemplary embodiment, slider 162 may include an external slider 1622 mounted slidably around main body 102, and an internal slider 1624 disposed slidably inside main body 102. In an exemplary embodiment, internal slider 1624 may be coupled to external slider 1622 in a way such that internal slider 1624 slides along a second axis responsive to a linear movement of external slider 1622 along the second axis. In an exemplary embodiment, the second axis may be the same as first axis 110.

In an exemplary embodiment, as shown in FIG. 3, lead screw 164 may include a cylindrical structure and lead screw 164 may be coupled to internal slider 1624. Furthermore, lead screw 164 may rotate about the second axis responsive to the linear movement of external slider 1622.

In an exemplary embodiment, internal slider 1624 may include an internally threaded section 1626 on an interior surface of internal slider 1624. In an exemplary embodiment, lead screw 164 may be disposed rotationally and slidably inside main body 102. Lead screw 164 may include an externally threaded section 1642 on an exterior surface of lead screw 164. In an exemplary embodiment, internally threaded section 1626 may be meshed with externally threaded section 1642. Furthermore, lead screw 164 may be configured to rotate around the second axis responsive to a linear movement of internal slider 1624 along the second axis.

In an exemplary embodiment, grasp encoder 166 may be coupled to lead screw 164. Furthermore, grasp encoder 166 may transmit a second set of data to processing unit 150. In an exemplary embodiment, the second set of data may include lead screw 164 rotation amount, lead screw 164 rotation rate, and lead screw 164 rotation direction. In an exemplary embodiment, external slider 1622 may include a hollow cylindrical-shaped structure. Similarly, internal slider 1624 may also include a hollow cylindrical-shaped structure. In an exemplary embodiment, external slider 1622 may be mounted slidably around second hollow cylindrical section 124. Furthermore, external slider 1622 may be configured to slide along first axis 110. In an exemplary embodiment, internal slider 1624 may be attached to external slider 1622 utilizing a plurality of screws 1628 through longitudinal slot 1242.

In an exemplary embodiment, the surgeon may slide external slider 1622 and grasp encoder 166 may determine amount, rate, and direction of lead screw 164 rotation and then may transmit the second set of data to processing unit 150 based on the amount, rate, and the direction of lead screw 164 rotation. Thereafter, processing unit 150 may transmit commands to surgical tool 120 associated with amount, rate, and direction of the grasp that surgical tool 120 may be supposed to do.

In an exemplary embodiment, grasp encoder 166 may be coupled to lead screw 164 utilizing a cylindrical-shaped coupling 168. In an exemplary embodiment, cylindrical-shaped coupling 168 may include a lead screw insertion hole 1682 located at a proximal end of cylindrical-shaped coupling 168 and a grasp encoder insertion hole 1684 located at a distal end of cylindrical-shaped coupling 168. In an exemplary embodiment, a size of lead screw insertion hole 1682 may correspond to a size of lead screw 164, and a size of grasp encoder insertion hole 1684 may correspond to a size of grasp encoder 166.

In an exemplary embodiment, an exemplary force feedback system may allow feedback to be received from surgical tool 120 indicating that surgical tool 120 has come in contact with, for example, patient tissue and this information may be passed along to master robot 130 so the surgeon is able to sense such an occurrence. Accordingly, in an exemplary embodiment, an exemplary force feedback system includes elements on slave robot 140 and master robot 130 sides. In an exemplary embodiment, exemplary force feedback system may include one or more dynamometers (not illustrated) associated with surgical tool 120 on slave robot 140 measuring a magnitude and a direction of a couple, a magnitude, and a direction of a force applied to surgical tool 120. Data related to measurements by the one or more dynamometers may be sent to processing unit 150, which may then provide commands to handle 101 (part of master robot 130) that reflects movement or impact based on the data related to measurements utilizing the one or more dynamometers. In an exemplary embodiment, elements of exemplary force feedback system which includes handle 101 on master robot 130 may include a roll actuator 149 coupled to roller 144, and a grasp actuator 169 coupled to lead screw 164. In an exemplary embodiment, responsive to a rotational movement of roll actuator 149, knob 142 thereby rotates around first axis 110, and responsive to a rotational movement of grasp actuator 169, external slider 1622 thereby moves linearly along the second axis.

In further detail, processing unit 150 may transmit a third set of data (commands) to roll actuator 149 based on the magnitude and the direction of the couple measured utilizing the one or more dynamometers and also roll actuator 149 may transmit a fourth set of data to grasp actuator 169 based on the magnitude and the direction of the force measured utilizing the one or more dynamometers. For purpose of reference, it may be understood that, during a surgery, various forces and couples may be applied to surgical tool 120. For example, in some exemplary embodiments, surgical tool 120 may be a tool for grasping tissues in body. Then, the disclosed haptic handling system may be utilized to provide two degrees of freedom for surgical tool 120: a roll degree of freedom and a grasp degree of freedom. Accordingly, in some exemplary embodiments, the force that is measured utilizing the one or more dynamometers may be the same as a force applied to interior side of jaws of the surgical tool from the grasped tissue. Also, in an exemplary embodiment, the couple that is measured utilizing the one or more dynamometers may be the same as a couple applied to the surgical tool from body organs during rotation of the surgical tool.

Figure 5:
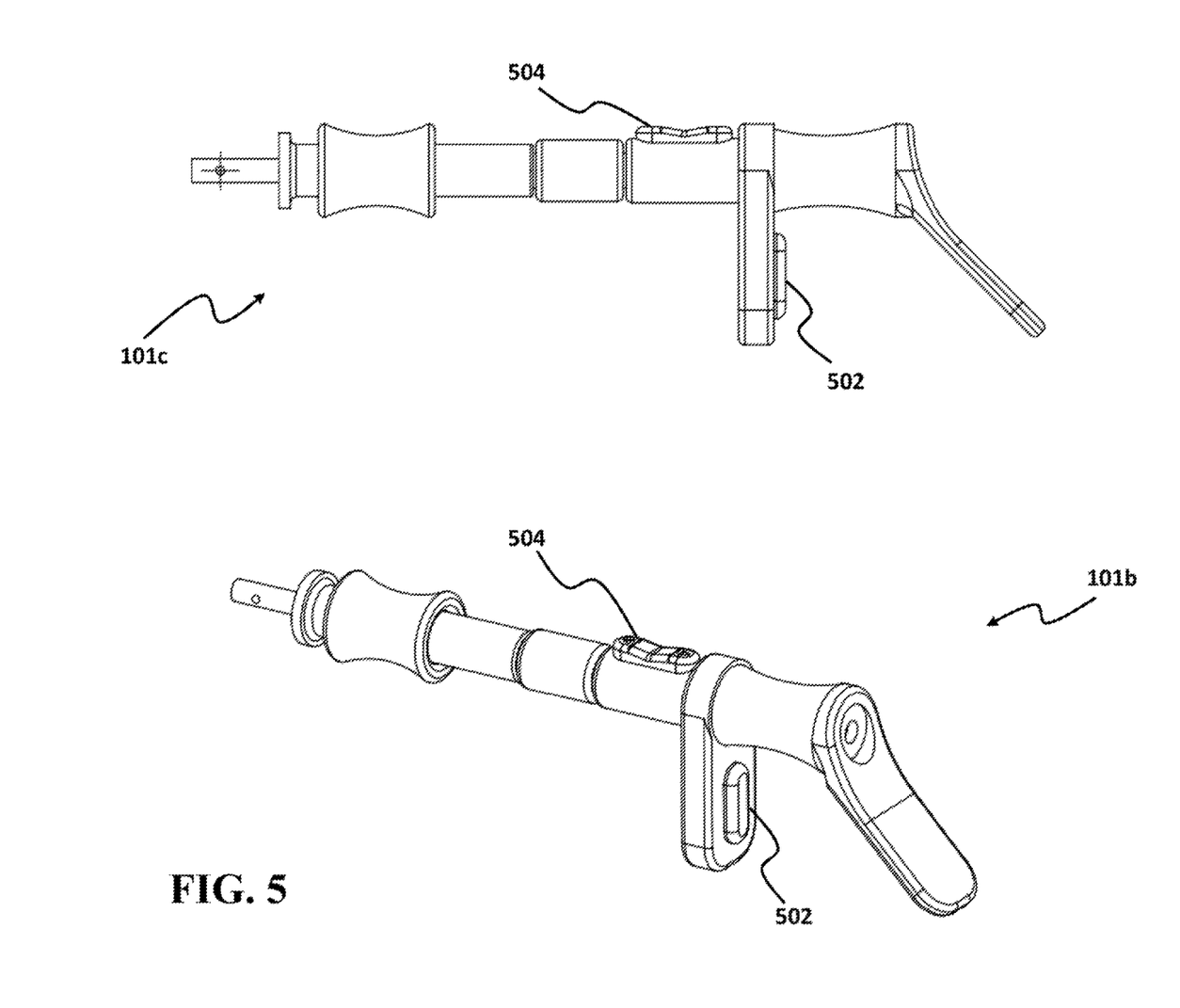
FIG. 5 illustrates a perspective view and a sectional view of a handle for a tele-robotic surgery, consistent with one or more exemplary embodiments of the present disclosure.

FIG. 5 shows a perspective view and a side view of handle 101 for a tele-robotic surgery, consistent with an exemplary embodiment of the present disclosure. As shown in FIG. 5, perspective view 101b of handle 101 and side view 101c of handle 101 illustrated that handle 101 may further include a check switch 502, and a multi-function switch 504. In an exemplary embodiment, check switch 502 may be configured to ensure that the surgeon holds the handle. Benefits from check switch 502 may include but are not limited to increased safety for the surgery operation. In an exemplary embodiment, multi-function switch 504 may activate electrocautery or insufflation and/or settings different system settings as needed. Benefits from multi-function switch 504 may include, but are not limited to, increased maneuverability for the surgeon during the surgery operation.

Figure 6:
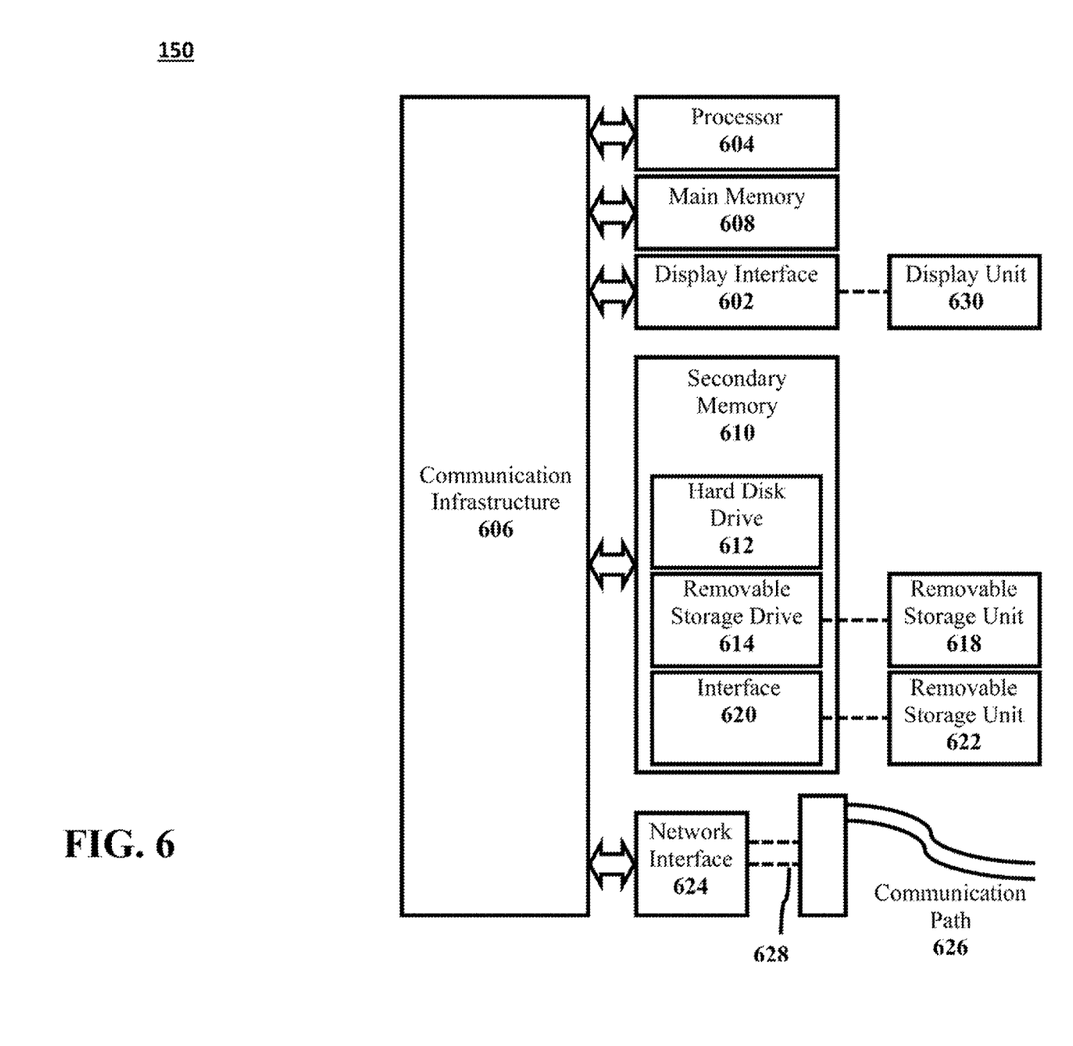
FIG. 6 illustrates an exemplary embodiment of a processing unit, consistent with one or more exemplary embodiments of the present disclosure.

FIG. 6 illustrates an exemplary embodiment of processing unit 150 in which an exemplary embodiment of the present disclosure, or portions thereof, may be implemented as computer-readable code, consistent with one or more exemplary embodiments of the present disclosure. For example, an exemplary tele-robotic surgical system may be implemented in processing unit 150 using hardware, software, firmware, tangible computer readable media having instructions stored thereon, or a combination thereof and may be implemented in one or more computer systems or other processing systems.

If programmable logic is used, such logic may execute on a commercially available processing platform or a special purpose device. One of ordinary skill in the art may appreciate that an exemplary embodiment of the disclosed subject matter can be practiced with various computer system configurations, including multi-core multiprocessor systems, minicomputers, mainframe computers, computers linked or clustered with distributed functions, as well as microcontrollers, pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An exemplary embodiment of the present disclosure is described in terms of this example processing unit 150. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 604 may be a special purpose or a general-purpose processor device. As will be appreciated by persons skilled in the relevant art, processor device 604 may also be a single processor in a multi-core/multiprocessor system, such system operating alone, or in a cluster of computing devices operating in a cluster or server farm. In an exemplary embodiment, processor device 604 may be connected to a communication infrastructure 606, for example, a bus, message queue, network, or multi-core message-passing scheme.

In an exemplary embodiment, processing unit 150 may also include a main memory 608, for example, random access memory (RAM), and may also include a secondary memory 610. In an exemplary embodiment, secondary memory 610 may include a hard disk drive 612, and a removable storage drive 614. In an exemplary embodiment, removable storage drive 614 may include a floppy disk drive, a magnetic tape drive, an optical disk drive, a flash memory, or the like. In addition, removable storage drive 614 may read from and/or write to a removable storage unit 618 in a well-known manner. In an exemplary embodiment, removable storage unit 618 may include a floppy disk, magnetic tape, optical disk, etc., which may be read by and written to by removable storage drive 614. As will be appreciated by persons skilled in the relevant art, removable storage unit 618 may include a computer usable storage medium having stored therein computer software and/or data.

In alternative implementations, secondary memory 610 may include other similar means for allowing computer programs or other instructions to be loaded into processing unit 150. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 which allow software and data to be transferred from removable storage unit 622 to processing unit 150.

In an exemplary embodiment, processing unit 150 may also include a communications interface 624. Communications interface 624 may allow software and data to be transferred between processing unit 150 and external devices. In an exemplary embodiment, communications interface 624 may include a modem, a network interface (such as an Ethernet card), a communications port, a PCM-CIA slot and card, or the like. Software and data transferred via communications interface 624 may be in the form of signals, which may be electronic, electromagnetic, optical, or other signals capable of being received by communications interface 624. These signals may be provided to communications interface 624 via a communications path 626. In an exemplary embodiment, communications path 626 may carry signals and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Computer program medium and computer usable medium may also refer to memories, such as main memory 608 and secondary memory 610, which may be memory semiconductors (e.g. DRAMs, etc.).

In some exemplary embodiment, computer programs (also called computer control logic) may be stored in main memory 608 and/or secondary memory 610. Computer programs may also be received via communications interface 624. Such computer programs, when executed, enable processing unit 150 to implement the present disclosure as discussed herein. In particular, the computer programs, when executed, may enable processor device 604 to implement the processes of the present disclosure. Accordingly, such computer programs represent controllers of processing unit 150. Where the present disclosure is implemented using software, the software may be stored in a computer program product and loaded into processing unit 150 using removable storage drive 614, interface 620, and hard disk drive 612, or communications interface 624.

Embodiments of the present disclosure may also be directed to computer program products including software stored on any computer useable medium. Such software, when executed in one or more data processing devices, causes a data processing device(s) to operate as described herein. An exemplary embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A haptic handling system for tele-robotic surgery, the haptic handling system comprising:
   one or more processors;
   a handle at a master robot comprising:
      a main body;
      a fine-tuning roll mechanism, comprising:
         a knob mounted rotatably around the main body;
         a roller coupled to the knob, the roller configured to rotate responsive to a rotation of the knob about a first axis, the knob configured to rotate about the first axis responsive to a rotation of the roller; and a roll encoder coupled to the roller, the roll encoder configured to transmit a first set of data based on the rotation of the knob to the one or more processors; and a grasp control mechanism, comprising:
   a slider, comprising:
      an external slider mounted slidably around the main body;
      an internal slider disposed slidably inside the main body, the internal slider coupled to the external slider, the internal slider configured to slide along a second axis responsive to a linear movement of the external slider along the second axis;
   a lead screw comprising a cylindrical structure, the lead screw coupled to the internal slider, the lead screw configured to rotate about the second axis responsive to the linear movement of the external slider, the external slider configured to slide along the second axis responsive to a rotational movement of the lead screw; and
   a grasp encoder coupled to the lead screw, the grasp encoder configured to transmit data based on the linear movement of the external slider to the one or more processors;

a roll actuator coupled to the roller, wherein responsive to a rotational movement of the roll actuator, the knob rotates around the first axis; and a grasp actuator coupled to the lead screw, wherein responsive to a rotational movement of the grasp actuator, the external slider moves linearly along the second axis; and a force feedback system comprising one or more dynamometers at a slave robot configured to measure a magnitude and a direction of a couple and also configured to measure a magnitude and a direction of a force applied to the surgical tool, wherein the one or more processors are further configured to:
   receive a set of couple data from the one or more dynamometers, the set of couple data comprising data associated with or related to the magnitude and the direction of the couple applied to the surgical tool;
   receive a set of force data from the second dynamometer, the set of force data comprising data associated with or related to the magnitude and the direction of the force applied to the surgical tool;
   transmit a second set of data to the roll actuator comprising commands associated or related to movement of the knob based on the set of couple data; and
   transmit a third set of data to the grasp actuator comprising commands associated or related to movement of the external slider based on the set of force data.

2. The haptic handling system of claim 1, wherein the main body comprises:
a first hollow cylindrical section comprising a hollow cylindrical-shaped structure and a sectoral slot on a shell of the first hollow cylindrical section; and
a second hollow cylindrical section comprising a hollow cylindrical-shaped structure and a longitudinal slot on a shell of the second hollow cylindrical section, the first hollow cylindrical section attached to the second hollow cylindrical section.

3. The haptic handling system of claim 2, wherein the knob comprising a hollow cylindrical structure, the knob mounted rotatably around the first cylindrical section and the knob configured to rotate about the first axis.

4. The haptic handling system of claim 3, wherein:
the roller comprising a first cylindrical section and a second cylindrical section, the first cylindrical section connected to the second cylindrical section utilizing a connecting rod;
the first cylindrical section disposed rotatably inside the sectoral slide, the first cylindrical section configured to rotate around a longitudinal axis of the roller; and
the first cylindrical section frictionally engaged with an interior surface of the knob.

5. The haptic handling system of claim 2, wherein
the external slider comprising a hollow cylindrical-shaped structure;
the internal slider comprising a hollow cylindrical-shaped structure;
the external slider mounted slidably around the second hollow cylindrical section, the external slider configured to slide along the first axis; and
the internal slider attached to the external slider utilizing a plurality of screws through the longitudinal slot.

6. The haptic handling system of claim 2, wherein the first axis corresponds to a longitudinal axis of the cylindrical-shaped structure of the first hollow cylindrical section.

7. The haptic handling system of claim 2, wherein the second axis corresponds to a longitudinal axis of the cylindrical-shaped structure of the second hollow cylindrical section.

8. The haptic handling system of claim 2, wherein the second axis is the same as the first axis.

9. The haptic handling system of claim 1, wherein:
the internal slider comprising an internally threaded section on an interior surface of the internal slider;
the lead screw disposed rotationally and slidably inside the main body, the lead screw configured to rotate around the second axis responsive to a linear movement of the internal slider along the second axis and the internal slider moving linearly along the second axis responsive to a rotational movement of the lead screw, the lead screw comprising an externally threaded section on an exterior surface of the lead screw, the internally threaded section configured to mesh with the externally threaded section.

10. The haptic handling system of claim 1, wherein the grasp encoder is coupled to the lead screw utilizing a cylindrical-shaped coupling, the cylindrical-shaped coupling comprising a lead screw insertion hole located at a proximal end of the cylindrical-shaped coupling and a grasp encoder insertion hole located at a distal end of the cylindrical-shaped coupling, a size of the lead screw insertion hole corresponding to a size of the lead screw, and a size of the grasp encoder insertion hole corresponding to a size of the grasp encoder.

11. A handle for tele-robotic surgery, the handle comprising:
a main body;
a fine-tuning roll mechanism, comprising:
   a knob mounted rotatably around the main body;
   a roller coupled to the knob, the roller configured to rotate responsive to a rotation of the knob about a first axis; and a roll encoder coupled to the roller, the roll encoder configured to transmit a first set of data associated with the rotation of the knob to one or more processors; and a grasp control mechanism, comprising:
  a slider, comprising:
    an external slider mounted slidably around the main body;
    an internal slider disposed slidably inside the main body, the internal slider coupled to the external slider, the internal slider configured to slide along a second axis responsive to a linear movement of the external slider along the second axis;
  a lead screw comprising a cylindrical structure, the lead screw coupled to the internal slider, the lead screw configured to rotate about the second axis responsive to the linear movement of the external slider; and
  a grasp encoder coupled to the lead screw, the grasp encoder configured to transmit a second set of data associated with the linear movement of the external slider to the one or more processors.

12. The handle of claim 11, wherein the main body comprises:
  a first hollow cylindrical section comprising a hollow cylindrical-shaped structure and a sectoral slot on a shell of the first hollow cylindrical section; and
  a second hollow cylindrical section comprising a hollow cylindrical-shaped structure and a longitudinal slot on a shell of the second hollow cylindrical section, the first hollow cylindrical section attached to the second hollow cylindrical section.

13. The handle of claim 12, wherein the knob comprising a hollow cylindrical structure, the knob mounted rotatably around the first cylindrical section, the knob configured to rotate about the first axis.

14. The handle of claim 13, wherein:
  the roller comprising a first cylindrical section and a second cylindrical section, the first cylindrical section connected to the second cylindrical section utilizing a connecting rod;
  the first cylindrical section disposed rotatably inside the sectoral slide, the first cylindrical section configured to rotate around a longitudinal axis of the roller; and
  the first cylindrical section frictionally engaged with an interior surface of the knob.

15. The handle of claim 12, wherein:
  the external slider comprising a hollow cylindrical-shaped structure;
  the internal slider comprising a hollow cylindrical-shaped structure;
  the external slider mounted slidably around the second hollow cylindrical section, the external slider configured to slide along the first axis; and
  the internal slider attached to the external slider utilizing a plurality of screws through the longitudinal slot.

16. The handle of claim 12, wherein the first axis corresponds to a longitudinal axis of the cylindrical-shaped structure of the first hollow cylindrical section.

17. The handle of claim 12, wherein the second axis corresponds to a longitudinal axis of the cylindrical-shaped structure of the second cylindrical section.

18. The handle of claim 12, wherein the second axis is the same as the first axis.

19. The handle of claim 11, wherein:
  the internal slider comprising an internally threaded section on an interior surface of the internal slider; and
  the lead screw disposed rotationally and slidably inside the main body, the lead screw configured to rotate around the second axis responsive to a linear movement of the internal slider along the second axis, the lead screw comprising an externally threaded section on an exterior surface of the lead screw, and the internally threaded section configured to mesh with the externally threaded section.

20. The handle of claim 11, wherein the grasp encoder is coupled to the lead screw utilizing a cylindrical-shaped coupling, the cylindrical-shaped coupling comprising a lead screw insertion hole located at a proximal end of the cylindrical-shaped coupling and a grasp encoder insertion hole located at a distal end of the cylindrical-shaped coupling, a size of the lead screw insertion hole corresponding to a size of the lead screw, and a size of the grasp encoder insertion hole corresponding to a size of the grasp encoder.

\* \* \* \* \*